United States Patent
Saita et al.

[11] Patent Number: 6,063,029
[45] Date of Patent: May 16, 2000

[54] DIAGNOSTIC PATCH AND METHOD FOR DIAGNOSIS USING THE SAME

[75] Inventors: Masaru Saita; Yuji Shimozono; Shigeo Ohta; Keishi Yonemura; Mizue Mukai; Akira Okayama, all of Tosu; Shuhei Imayama, Fukuoka, all of Japan

[73] Assignee: Hisamitsu Pharmaceutical Co., Inc., Tosu, Japan

[21] Appl. No.: 08/454,113

[22] PCT Filed: Nov. 29, 1993

[86] PCT No.: PCT/JP93/01737

§ 371 Date: Apr. 29, 1996

§ 102(e) Date: Apr. 29, 1996

[87] PCT Pub. No.: WO94/13209

PCT Pub. Date: Jun. 23, 1994

[30] Foreign Application Priority Data

Dec. 7, 1992 [JP] Japan ................................. 4-351171
Dec. 16, 1992 [JP] Japan ................................. 4-353901

[51] Int. Cl.[7] .................................................. A61B 5/00
[52] U.S. Cl. ........................... 600/309; 600/362; 600/573; 600/584
[58] Field of Search ................................ 128/632, 636, 128/760, 771; 129/637

[56] References Cited

U.S. PATENT DOCUMENTS

| | | |
|---|---|---|
| 4,788,971 | 12/1988 | Quisno . |
| 4,836,217 | 6/1989 | Fischer . |
| 5,203,327 | 4/1993 | Schoendorfer et al. ............ 128/636 X |
| 5,219,762 | 6/1993 | Katamine et al. ..................... 436/518 |

FOREIGN PATENT DOCUMENTS

| | | |
|---|---|---|
| 0376133 | 7/1990 | European Pat. Off. . |
| 9203731 | 3/1992 | WIPO . |

*Primary Examiner*—Robert L. Nasser
*Assistant Examiner*—Ryan Carter
*Attorney, Agent, or Firm*—Bucknam and Archer

[57] ABSTRACT

A diagnostic patch comprising at least an adsorption carrier adsorbing a substance secreted from a living body, which is useful particularly for the diagnosis of mammary cancer or atopic dermatitis, and a method for the diagnosis of mammary cancer or atopic dermatitis with said preparation.

18 Claims, 1 Drawing Sheet

Adhesive bonding type

< Two – layer >

FIG. 1 (a)

Seperation type

< Two – layer >

FIG. 1 (b)

< One – layer >

FIG. 1 (c)

< Incorporation >

FIG. 1 (d)

DIAGNOSTIC PATCH AND METHOD FOR DIAGNOSIS USING THE SAME

TECHNICAL FIELD

The present invention relates to a diagnostic patch which has various functions and is suitably used particularly for the diagnosis of mammary cancer or atopic dermatitis, and a method for the diagnosis of mammary cancer or atopic dermatitis with said patch.

BACKGROUND OF THE PRIOR ART

Various methods have been employed in the checkup or diagnosis of diseases. For example, biochemical or biological examination is carried out by collecting blood invasively and conducting diagnosis based on the components, diagnostic markers and cells contained in the blood; pathological examination is conducted by conducting the biopsy of cancer tissue or the examination for abnormality on cellular level invasively; and the examination of urine, stool or saliva involves the collection thereof. In carrying out these method, a doctor, nurse or clinical analyst must collect blood with a syringe, must extirpate a tissue (affected site) from a living body with a sharp-edged knife or must collect an object of examination or diagnosis in a special case in cooperation with a patient.

In particular, mammary cancer is known to be a cancer which is difficult to find in an early stage, though it is one of the major cancers which tend to increase. Although the diagnosis of mammary cancer is conducted by internal examination, palpation, mammography (X ray), detection of tumor markers [such as carcinoembryonic antigen (CEA), α-fetoprotein (AFP), cancer antigen (CA15-3) and various saccharide antigens], ultrasonography or the like, these methods do not always exhibit a high diagnosis efficiency. For example, a phyma-free cancer gives neither pain nor subjective symptoms in early stages, so that patients therewith cannot find abnormality in many cases. Meanwhile the diagnosis based on a tumor marker such as CEA, CA15-3 or AFP is conducted by determining the concentration thereof in blood by radioimmunoassay (RIA) or enzyme immunoassay (EIA) and the concentration of such a tumor marker in blood serves as an indication of the prognosis or therapy effect of a cancer which is advanced considerably or metastasizing to the lymph node. However, it is very difficult to conduct the early diagnosis of primary mammary cancer by determining the concentration, because the positive rate for an early cancer is extremely low.

There were therefore many cases wherein the cancer had been advanced or had metastasized to the lymph node with the result of unwilling mastectomy.

Accordingly, the early diagnosis of mammary cancer is little conducted by the assay of concentration of a tumor marker in blood, but depends on palpation or inquiry. Further, the diagnosis with X ray (such as mammography) involves the exposure of a living body to a considerably high dose of X ray and the reading of a mammograph necessitates much experience and high skill. Further, cytodiagnosis involves the determination of a questionable site. However, it is difficult to find an extremely small affected site by current methods easily and simply.

The assay of specific substances contained in a serum, blood or biopsy specimen is generally conducted by a physiochemical or biochemical method, immuno-assay, a pathological method or the like. Therefore, the assay cannot be conducted at the site of medical services, so that the above specimen must be entrusted to an institution fitted with examination equipment or a special laboratory technician. Accordingly, it takes many days to know the result of the assay, which is problematic particularly in cases necessitating immediate treatment.

On the other hand, atopic dermatitis is steadily increasing owing to change in the living environment, lowering in the adaptation of a living body and lowering in the natural immunity, becoming a socially significant problem. In particular, atopic diseases are extremely prevalent, so that it is said that there are one or two (latent) patients therewith per ten persons in Japan. However, the cause of the diseases has not sufficiently been elucidated as yet and the diagnosis and therapy of them depend on the macroscopic or experimental sense of a doctor in many cases.

Blood specimen collection or biopsy is problematic to patients in that the use of a needle of injection, a syringe, a sharp-edged knife or radiation gives greater or lesser fear or pain and the patients must go to a suitable institution. Further, the assay of urine or stool is disadvantageous in that the place and behavior for collecting it are limited.

Meanwhile, there have already been known (1) medical patches containing drugs, e.g., salicylic anti-inflammatory agent or angina pectoris remedy such as nitroglycerin; diagnostic patches useful in the patch test for skin irritation; and those which are useful in the detection of allergen for determining the sensitizer of allergic dermatitis or the like (all of these patches are characterized by releasing a drug or other substance) and (2) pads for capturing the blood or exudate discharged from a living body or for disinfecting wound, for example, gauze, pad for wound and sanitary napkin. However, there has not been known any diagnostic patches which can effectively trap a substance or liquid discharged from the skin or mucosa and on which the assay of the substance or liquid can be conducted. In particular, there has not known any idea of applying a patch directly to the skin and the breast including the nipple and conducting the assay on the patch.

It has been known that various biocomponents are secreted from the skin or mucosa. However, the amount of an object for the assay secreted from the skin is very small and the sampling of a liquid on the skin is difficult, though the assay of a liquid substance secreted from the skin according to the prior art involves the pipetting of the liquid substance. For these reasons, there has been no accurate method for assaying a liquid substance secreted from the skin qualitatively or quantitatively has been found.

Further, it has also been known that a (liquid) secretion is discharged from the nipple as observed in the case of papillary hypersecretion. However, the sampling and assay of the secretion were problematic. It was reported in Inaji et al., "Igaku no Ayumi (Advance in Medicine)", 134, 575, 1985 that the secretion from the nipple was pipetted and examined for CEA by immunoassay, and as a result, CEA was found to be useful in the diagnosis for cancer.

Further, Mochida et al. reported in Japanese Patent Laid-Open Gazette Nos. 250069/1989, 176466/1990 and 280061/1990 that a secretion from the nipple can be analyzed for a tumor-associated antigen (such as CEA) qualitatively or semiquantitatively by sampling a slight amount of a secretion from the nipple and dropping it onto a liquid-nonpermeable sheet on which a specific antibody against the antigen is immobilized. However, this method involves the pipetting of a secretion from the nipple and the application of the secretion on a liquid-nonpermeable sheet (solid phase), so that it has a problem of being applicable only to a patient with papillary hypersecretion wherein the amount of secretion from the nipple is about 0.2 to 50 μl. Further, these patent documents disclose a vague idea of detecting CEA by bringing a sheet having a CEA-specific antibody immobilized thereon into contact with the nipple, but are silent on the specific technique or method for carrying out such detection. In particular, they are completely silent on the idea of detecting CEA or other objective substance by applying a diagnostic patch which comprises a liquid-permeable adsorption carrier and a water-absorbing and adsorbent membrane to capture and immobilize a secretion which cannot be detected as a liquid at least macroscopically.

SUMMARY OF THE INVENTION

The present invention aims at solving the problems of the Prior art to provide a diagnostic patch with which the diagnosis of mammary cancer, atopic dermatitis or the like can be easily conducted in a short time in a noninvasive manner without limiting the place of diagnosis, and a method for the diagnosis with said patch.

Detailed objects of the present invention are as follows:

(1) to provide a diagnostic patch for mammary cancer or atopic dermatitis which enables the sampling free from invasion into the body of a patient and use of a special pipette for sampling a body fluid and gives neither fear nor pain nor uncomfortableness to a patient and with which many samples can be assayed and judged, (2) to provide a method for the diagnosis of mammary cancer or atopic dermatitis by which results can be given in a short time and a doctor or nurse can speedily and easily conduct assay and judgement at the site of medical service and which does not limit the place of sticking and peeling, examiner and the place of examination, (3) to provide a method for the diagnosis of mammary cancer with said patch by which a secretion from the nipple, particularly a tumor marker can be specifically assayed and which is useful as an auxiliary means for the diagnosis of mammary cancer either with or without phyma, and (4) to provide a method for the diagnosis of atopic dermatitis with said patch, by which the amount of secretary Immunogloburin A (sIgA) resulting from the skin can be determined and which is useful as an auxiliary means for the diagnosis of atopic dermatitis.

The above objects can be attained by making a diagnostic patch having at least a liquid-permeable adsorption carrier.

Further, the diagnosis of mammary cancer can be attained by making a very slight amount of a papillary secretion which is contained in a fluid discharged from the nipple at least in an amount unrecognizable as liquid at least macroscopically (of course, too small an amount to be sampled by pipetting or the like), and which is useful for the diagnosis of the cancer adsorbed and immobilized on the diagnostic patch, and conducting the assay of the substance.

Furthermore, the diagnosis of atopic dermatitis can be attained by making a very slight amount of sIgA contained in a fluid discharged from the skin at least in an amount unrecognizable as liquid at least macroscopically (of course, too small an amount to be sampled by pipetting or the like) adsorbed and immobilized on the diagnostic patch and conducting the assay thereof immunologically.

Namely, the diagnostic patch of the present invention is characterized by comprising at least an adsorption carrier for adsorbing a substance secreted from a living body (e.g., a papillary secretion discharged from the nipple in the diagnosis of mammary cancer or a slight amount of secretary immunogloburin A secreted from the skin in the diagnosis of atopic dermatitis) and is suitably used for the diagnosis of mammary cancer or atopic dermatitis. The method for the diagnosis according to the present invention is characterized by assaying an objective substance which is secreted from a living body and is useful for diagnosis with the above diagnostic patch.

The diagnostic patch of the present invention will now be described in detail.

The material to be used in the present invention as the support includes paper, cloth, nonstretch and stretch films made of various resins (such as polyester resin, silicone resin, urethane resin, polyethylene resin, ethylene-vinyl acetate copolymer and flexible polyvinyl chloride), aluminum foil and composite materials composed of two or more of them. Among these materials, the use of a translucent or transparent one is desirable in easiness in the check of site of application of the patch and affected site and convenience and simple means to be used in examination.

The pressure-sensitive adhesive to be used in the present invention may be a substance which exhibits pressure-sensitive adhesion or adhesion properties and does not exert any adverse effect on the skin when applied to a human body. Since the examination according to the present invention is carried out on the diagnostic patch after the application and peeling of the preparation, it is preferable that the pressure-sensitive adhesive be one which has a function of readhering to other fixing device, which does not hinder the adsorption of an objective substance on the adsorption carrier, and/or which does not exert any influence on the final examination and reaction. Further, it is preferable from the standpoint of easiness in the check of site of application of the preparation that the pressure-sensitive adhesive be one which can give a translucent or transparent pressure-sensitive adhesive tape when combined with the support. The pressure-sensitive adhesive generally comprises a pressure-sensitive adhesive component and other additives such as a tackifier and softener. The pressure-sensitive adhesive may be spread over the whole or one or more parts of the surface of the support. Specific examples of the components constituting the pressure-sensitive adhesive will now be described, though the components are not limited to them.

The pressure-sensitive adhesive component includes natural and synthetic resins such as natural rubber, polyisobutylene rubber, polybutadiene rubber, silicone rubber, polyisoprene rubber, styreneisopropylenestyrene block copolymer (hereinafter abbreviated to "SIS") and acrylate copolymer, which are used in the present invention either alone or as a mixture of two or more of them. The content of the pressure-sensitive adhesive component(s) in the pressure-sensitive adhesive may range from 10 to 50% by weight, preferably from 15 to 45% by weight, still preferably from 20 to 40% by weight.

The tackifier to be used for adjusting the pressure-sensitive adhesiveness includes rosin, hydrogenated rosin and esters thereof, polyterpene resin, petroleum resin and ester gum, etc. which are used either alone or as a mixture of two or more of them. The content of the tackifier(s) in the pressure-sensitive adhesive may be up to 40% by weight, and preferably ranges from 5 to 35% by weight, still preferably from 15 to 30% by weight.

Further, the softener to be used in the present invention may be one or more members selected from among liquid paraffin, polybutene, liquid polyiso-butylene and animal and vegetable oils. The content of the softener(s) in the pressure-sensitive adhesive may range from 5 to 60% by weight, preferably from 10 to 50% by weight, still preferably from 25 to 45% by weight.

If necessary, the pressure-sensitive adhesive may further contain one or more fillers selected from among titanium dioxide, synthetic aluminum silicate, zinc oxide, calcium carbonate, starch acrylate, silica and so forth. The content of the filler(s) in the pressure-sensitive adhesive may be up to 5% by weight, and preferably ranges from 0.1 to 4% by weight, still preferably 1 to 3% by weight.

Further, one or more absorbent polymers selected from among polyacrylic salts, starch-acrylic acid graft copolymer and so forth may be added to the pressure-sensitive adhesive for the purpose of imparting water absorption properties to the preparation or protecting the skin from rash. Specific examples of the absorbent polymer include Sanwet IM-300, IM-1000 and IM-1000MPS (products of SANYO CHEMICAL INDUSTRIES, LTD., trade name), AquaKeep 4S and 4SH (products of SEITETSU KAGAKU CO., LTD., trade name), SumiKagel SP-520 and N-100 (products of SUMITOMO CHEMICAL COMPANY, LIMITED, trade name) and Arasov 800 and 800F (products of ARAKAWA CHEMICAL INDUSTRIES, LTD.).

Further, an antioxidant such as dibutylhydroxy-toluene may be added to the pressure-sensitive adhesive in an amount of 3% by weight or below as needed.

If necessary, a drug such as an antihistamic or an anti-allergic agent may be further added to the pressure sensitive adhesive in a suitable amount for the purpose of protecting the skin from rash.

A tape comprising the above support and the above pressure-sensitive adhesive spread over the surface of the support (this tape is hereinafter referred to as "pressure-sensitive adhesive tape") exhibits high adhesiveness to the skin, so that the diagnostic patch of the present invention can be stuck on the skin without fail.

According to the present invention, an adsorption carrier is stuck directly on the above pressure-sensitive adhesive, incorporated into the pressure-sensitive adhesive as powder or stuck indirectly on the pressure-sensitive adhesive by bonding the carrier to a water-absorbing and adsorbent membrane with an adhesive and sticking the resulting composite on the pressure-sensitive adhesive, and exhibits a function of effectively adsorbing a substance contained in a fluid secreted from a living body, particularly, the skin, mucosa or nipple. Accordingly, the adsorption carrier according to the present invention is substantially composed of one or more liquid-permeable materials. When one kind of material is used as the adsorption carrier in a state incorporated into the pressure-sensitive adhesive or stuck on the pressure sensitive adhesive, the material must also have a water absorbing or retaining function which will be described below.

Examples of the material to be used as the adsorption carrier include cellulose derivatives such as cellulose, carboxymethylcellulose, carboxymethylcellulose salts, hydroxyethylcellulose, hydroxypropylcellulose, methylcellulose, ethylcellulose, carboxymethylethylcellulose, hydroxypropylmethylcellulose, ethylhydroxyethylcellulose, cellulose acetate, cellulose nitrate, cellulose acetate phthalate and hydroxypropylmethylcellulose phthalate; porous gels such as poly-2-hydroxyethyl methacrylate, polyacrylic acid and polyvinyl alcohol-polyacrylic acid composite; fibrous matrixes such as polyurethane, polyester, polyethylene, polyvinyl chloride, polyvinylidene fluoride and nylon; papers (such as nonwoven paper and filter paper); cloths (such as staple fiber, cotton, silk and synthetic fibers); and porous ceramics such as silica, alumina, titania, zirconia and ceria, which may be used either alone or as a mixture of two or more of them. The material to be used as the adsorption carrier is not limited to those described above, but may be any one exhibiting the above functions. It is preferable to use one of the above cellulose derivatives as the adsorption carrier.

In practice, the diagnostic patch of the present invention is used in a case of ordinary skin or the like wherein the fluid discharged therefrom cannot be recognized as liquid at least macroscopically, a case of sweated skin, the nipple with papillary hypersecretion or the like wherein the fluid discharged therefrom can be recognized as a small amount of liquid, and a case of urine, bleeding or the like wherein the fluid discharged can be recognized as a relatively large amount of liquid. The patch of the present invention must be applicable to all of these cases, so that it is preferable that the adsorption carrier be permeable to liquid.

The adsorption carrier is required to adsorb objective secreted substances as completely as possible even under any of the above various conditions. In order to fulfill the requirement, it is preferable to use a material having pores (such as hole or void) or a matrix material. (hereinafter, both the material are generally called "porous materials"). In other words, it is substantially preferable that the adsorption carrier have a large surface area. Further, it is necessary that the substance adsorbed on the carrier is not released from the carrier during examination.

The pore size of the adsorption carrier has an influence on the adsorption of a secreted substance on the carrier, the permeability of the carrier to a fluid discharged from a living body and the judgement and evaluation in examination and may be 0.01 to 100 $\mu$m, preferably 0.01 to 50 $\mu$m, still preferably 0.01 to 30 $\mu$m. When the pore size of the adsorption carrier is too small, the adsorption carrier will suffer from clogging, while when it is too large, the adsorption of an objective secreted substance on the carrier will be poor to result in difficult judgement. Thus, the pore size is one of the factors important to the diagnostic patch of the present invention. Among the above materials for the adsorption carrier, it is preferable that the cellulose derivative have a pore size of 0.01 to 50 $\mu$m, particularly preferably 0.01 to 30 $\mu$m.

According to the present invention, a water-absorbing and adsorbent membrane is incorporated in the above pressure-sensitive adhesive as powder, stuck directly on the pressure-sensitive adhesive or stuck directly on the pressure-sensitive adhesive in a state bonded to the adsorption carrier with adhesive. This water-absorbing and adsorbent member exhibits a function of absorbing the fluid remaining after the adsorption of an objective secreted substance or adsorbing the other secreted components (unnecessary for assay), that of stabilizing the dosage form of the patch, that of imparting air permeability to the patch to lower the stimulation to the skin, that of stabilizing the stain, that of preventing the fraction of the adhesion carrier present as the outermost layer (particularly when the carrier is made of an easily fractural material such as some cellulose derivative), and so forth.

This water-absorbing and adsorbent member serves as a suctorial driving force when the fluid discharged from a living body cannot be recognized as liquid at least macroscopically like in the case of ordinary skin, while the member deals with the residual fluid and/or the substances other than an objective one, when the fluid discharged can be recognized as a slight to large amount of liquid. Accordingly, it is preferable that the member be one having water absorption and retention properties and an adsorptive power of substances.

The water-absorbing and adsorbent member according to the present invention is substantially made of a material having a water-absorbing or retaining function and/or an adsorbent function. The material of the member includes highly water-absorptive resins in addition to the above materials for the liquid-permeable adsorption carrier. Specific examples of the material include high absorbent polymers such as polyacrylic acid and salts thereof, isobutylene-maleic acid copolymer, starch-acrylic acid graft copolymer, polyethylene oxide, saponified vinyl acetate-unsaturated dicarboxylic acid copolymer, carboxy-methylcellulose, saponified starch-acrylic acid graft copolymer and alginate; cellulose derivatives such as cellulose, carboxymethylcellulose, carboxymethyl-cellulose salts, hydroxyethylcellulose, hydroxy-propylcellulose, methylcellulose, ethylcellulose, carboxymethylethylcellulose, hydroxypropylmethylcellulose, ethylhydroxyethylcellulose, cellulose acetate, cellulose nitrate, cellulose acetate phthalate and hydroxypropylmethylcellulose phthalate; porous gels such as poly-2-hydroxyethyl methacrylate, polyacrylic acid and polyvinyl alcohol-polyacrylic acid composite; fibrous matrixes such as polyurethane, polyester, polyethylene and polyvinyl chloride; filter paper and cloths. One or more of these materials are used in the present invention, though the material of the member is not limited to them, but may be any one having the above function. When the adsorption carrier and the water-absorbing and adsorbent member are made of the same material, the amount, pore size, thickness and pretreatment of the material may be suitably changed between the carrier and the member.

When the diagnostic patch of the present invention is made by the use of an adsorption carrier and a water-absorbing and adsorbent membrane each in the form of a sheet, an adhesive is used in a position lying between the sheets to bond the sheets to each other wholly or partially. The adhesive is not particularly limited but may be any substance which exhibits adhesion properties and has no influence on judgement.

The adhesive is particularly preferably a hydrophilic substance and examples thereof include water-soluble cellulose derivatives such as carboxymethylcellulose, methylcellulose, hydroxyethylcellulose and hydroxypropylcellulose; polysaccharides such as alginic acid, guar gum, acacia, tragacanth and tamarind seed; and natural and synthetic polymers such as gelatin, polyacrylic acid, polyacrylic acid salts, polyvinyl alcohol, polyethylene oxide, isobutylene-maleic anhydride copolymer, methoxyethylene-maleic anhydride copolymer, water-soluble epoxy resin, water-soluble acrylic resin and water-soluble polyester. The use of such a hydrophilic adhesive is convenient to the absorption of the water remaining after the adsorption of an objective substance on the adsorption carrier by the water-absorbing and adsorbent member and the making of the preparation.

The peelable cover is not particularly limited but may be any one which can protect the adsorption carrier layer. Preferable examples thereof include release papers treated with release agents; and films of polymers such as cellophane, polyethylene, polypropylene, polyester, polyethylene terephthalate and so forth.

The form of the diagnostic patch of the present invention includes rectangle, circle, ellipse, regular square, heart, lozenge and so forth, though the form is not particularly limited, but may be any one suitable for practical use. Further, the size and color of the preparation are also not particularly limited but may be any ones suitable for practical use.

Figure 1:
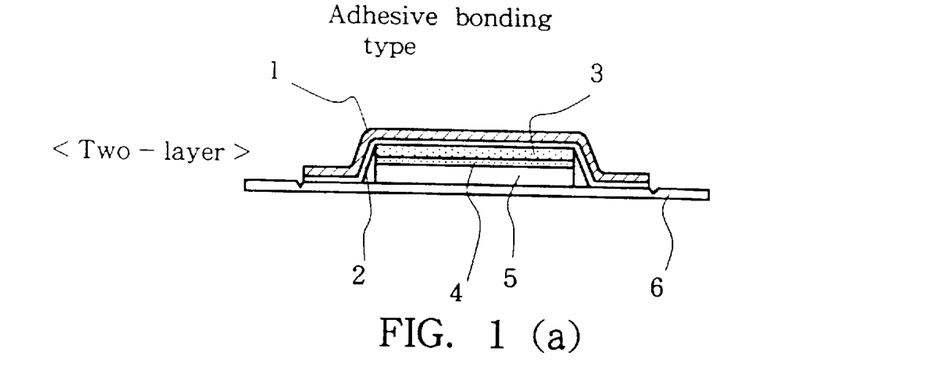
FIG. 1 is shematic sectional views showing the form and constitution of the diagnostic patch of the present invention specifically.

In order to fit the patch to an abnormal site, it is preferable that the pressure-sensitive adhesive tape according to the present invention be either translucent or transparent and an expression for discrimination is made on the support. The term "expression for discrimination" refers to a symbol, such as "up", "down", "L" and "R", printed or stamped on the support or a coloring made thereon, which makes it possible to discriminate whether to apply the patch to the right or left breast or which of the sides of the patch must be applied upward. The term "two-layer structure" refers to a structure wherein both an adsorption carrier 5 and a water-absorbing and adsorbent membranes 3 lie over a pressure-sensitive adhesive 2. This two-layer structure includes one of adhesive bonding type wherein an adhesive 4 lies between the carrier 5 and the member 3 (FIG. 1 (*a*)) and one of separation type wherein an adhesive 4 does not lie between them (FIG. 1 (*b*)). The term "one-layer structure" refers to a structure wherein an adsorption carrier 5 is applied on a pressure-sensitive adhesive 2. Further, the term "incorporation structure" refers to a structure wherein an adsorption carrier 5 is incorporated in a pressure-sensitive adhesive 2 as fine powder.

The method for the diagnosis of mammary cancer or atopic dermatitis according to the present invention will now be described.

First, the method for the diagnosis of mammary cancer according to the present invention is characterized by applying the above diagnostic patch to the breast including the nipple, making a papillary secretion adsorbed and immobilized on the adsorption carrier and conducting the assay of the substance.

As compared with contact methods other than the sticking method, the diagnostic patch of the present invention is characterized in that the patch can be fixed at an affected site in contact therewith for a desired time without fail, that even a macroscopically small amount of a fluid discharged from a living body can be assayed and that when used in the diagnosis of early mammary cancer (particularly one free from phyma), the primary site can be presumed.

According to the method of the present invention, the diagnostic patch is stuck on the breast for a predetermined time in such a way as to fit the center of the adsorption carrier layer to the nipple, by which an extremely small amount of a papillary secretion discharged from the nipple is adsorbed and immobilized on the adsorption carrier of the preparation. The term "papillary secretion" used in this description refers to a specific substance or protein secreted from the nipple or constituent peptide thereof.

Various tumor-associated antigens and tumor markers can be selected with respect to the papillary secretion thus immobilized. Examples of such antigens and markers include carcinoembryonic antigen (hereinafter abbreviated to "CEA"), melanoma cell, melanoma marker (NKI/C3), melanoma marker (PAL-M1), neuroblastoma (CE7) neuroblastoma (AD2), malignin, α-fetoprotein, pepsinogen, basic fetoprotein, panacreatic cancer fetal antigen fetoprealbumin, carbohydrate antigen (CA19-9), pancreatic cancel associated antigen (CA50), cancer antigen (CSLEX-1), pancreatic cancer associated antigen (Sialyl SSEA-1SLX), pancreatic cancer associated antigen (Du-pan-2), cancer antigen (erbB2), cancer antigen (NCC-ST-439), carbohydrate antigen (Sialyl Tn STN), cancer antigen (CA72-4), cancer antigen (KM-01), pancreatic cancer associated antigen (Span-1), carbohydrate antigen (CA125), cancer antigen (CA15-3), squamous cell carcinoma (SCC), seminoprotein (γ-Sn), prostata-specific antigen (PA), ferritin, tissue polypeptide antigen (TPA), immune acid protein (IAP), immunosuppressive acid protein, prostatic acid protein (PAP), neuron-specific enolase (NSE), blood, enzyme (particularly, POD and ALP), amino acids (particularly Ala and Glu), mucous substances and various hormones.

According to the present invention, these tumor-associated antigens and tumor markers can be assayed quantitatively, semiquantitatively or qualitatively by antigen-antibody reaction, chemical reaction or enzyme reaction.

Among the above tumor-associated antigens and tumor markers, CEA will now be described as a representative example. CEA is a glycoprotein comprising 668 amino acid units and containing about 50% of sugar and is one of clinically useful carcinoembryonic tumor associated antigens. It is said that the blood CEA concentration increases with the worsening of colic cancer or other cancer. However, the determination of blood CEA concentration has been conducted mainly for the purpose of checking post-operative progress or the therapeutic effect of a drug, because the transfer of CEA from cancer tissue to blood occurs for the first time when a cancer has pretty been advanced. Therefore, it has a great clinical meaning to enable the determination of amount of CEA at a site affected by a localized cancer which is not accompanied with the transfer of CEA resulting from a cancer tissue to blood or lymph or which exhibits only a blood CEA concentration lower than the measurable lowest one (i.e., so-called early cancer free from phyma). The same may apply to other markers. According to the present invention, the assay of CEA can be conducted by applying the diagnostic patch for mammary cancer to the nipple.

In the assay of CEA, anti CEA monoclonal antibody or polyclonal antibody can be used in consideration of specificity and sensitivity. The antibody may be any one exhibiting high sensitivity and specificity to CEA. The diagnostic patch is stuck on an affected site, allowed to stand as such for a predetermined time and peeled and thereafter is assayed with such an antibody by EIA, immunochromatography, immunoassay using a latex-bound antibody, immunoassay using a gold colloid-bound antibody or fluorescent or luminescent immunoassay. As a result, the CEA secreted from the nipple can be detected as a deeply stained image of dot (spot) or spread form at the position corresponding to the primary site of a cancer.

The extent of advance of the cancer, the range thereof and which of mammary glands secretes CEA can be judged qualitatively, semiquantitatively or quantitatively based on the density, size and position of the stained image with the naked eye, a microscope or a densitograph.

Then, the method for the diagnosis of atopic dermatitis according to the present invention will now be described.

The method for the diagnosis of atopic dermatitis according to the present invention is characterized by sticking the above sticking type patch for the diagnosis of atopic dermatitis on the skin, mucosa or affected site of a human body to make a secretion therefrom adsorbed and immobilized on the adsorption carrier, and analyzing the accretion of sIgA by immunoassay.

According to the present invention, the stickingtype preparation for the diagnosis of atopic dermatitis is stuck on the skin, mucosa or affected site of a human body and allowed to stand as such for a predetermined time, for example, one minute to 30 hours, by which a secretion from the skin or the like is adsorbed and immobilized on the adsorption carrier. The term "secretion" used in this case refers to a fluid discharged along sweat gland and may contain sIgA, the amount of which may be either recognizable or unrecognizable as liquid macroscopically. In the present invention, the amount of sIgA is selectively determined by immunoassay. As a result of the assay, deeply stained images of dot form are found at sites corresponding to the sweat glands of the skin.

BRIEF DESCRIPTION OF THE DRAWING

FIGS. 1 (a) to (d) show the schematic sectional views of representative preparations according to the present invention (wherein the forms and constitution thereof are illustrated). In these Figs, numeral 1 refers to a support; numeral 2 a pressure-sensitive adhesive; numeral 3 a water-absorbing and adsorbent membrane; numeral 4 an adhesive; numeral 5 an adsorption carrier; and numeral 6 a peelable cover.

FIGS. 1 (a) and (b) show preparations of two-layer structure;

FIG. 1 (c) shows a preparation of one-layer structure; and

FIG. 1 (d) shows a preparation of incorporation structure.

BEST MODE FOR CARRYING OUT THE INVENTION

The present invention will now be described specifically by referring to the following Examples.

Hereinafter, the term "diagnostic patch" refers to that of a final dosage form; the term "pressure-sensitive adhesive tape" refers to one comprising a support and a pressure-sensitive adhesive; the term "two-layer adsorption carrier (of adhesive bonding type)" refers to a carrier wherein an adsorption carrier and a water-absorbing and adsorbent membrane are adhesive-bonded to each other; the term "two-layer adsorption carrier (of separation type)" refers to a carrier wherein an adsorption carrier and a water-adsorbing or adsorbent member lie in contact with each other but separately; the term "one-layer adsorption carrier" refers to a carrier stuck on a pressure-sensitive adhesive directly; and the term "incorporation-type adsorption carrier" refers to a carrier incorporated in a pressure-sensitive adhesive as powder. In Table 1, all parts are by weight.

EXAMPLE 1

Diagnostic Patch having Two-Layer Adsorption Carrier of Adhesive Bonding Type

An elliptic pressure-sensitive adhesive tape (3 cm×4 cm) was made by spreading a pressure-sensitive adhesive comprising SIS, polyisobutylene, ester gum and liquid paraffin (at a weight ratio of 20:10:35:35) on a flexible stretch film of polyvinyl chloride as a support.

Separately, a two-layer adsorption carrier was made by bonding microporous cellulose ester (pore size: 0.6 μm, a product of Millipor) as a water-absorbing and adsorbent membrane to cellulose nitrate/cellulose acetate (pore size: 0.45 μm, a product of Millipor) as an adsorption carrier with a polyacrylate copolymer. The obtained two-layer adsorption carrier was cut into a circle having a diameter of 1.5 cm. The resulting circular carried was stuck on the above pressure-sensitive adhesive tape through the water-absorbing and adsorbent membrane. The carrier surface of the resulting composite was covered with a polyethylene terephthalate film to give a diagnostic patch.

EXAMPLE 2
Diagnostic Patch having Two-Layer Adsorption Carrier of Separation Type A circular pressure-sensitive adhesive tape having a diameter of 3 cm was made by spreading a pressure-sensitive adhesive comprising SIS, polyisobutylene, ester gum and liquid paraffin (at a weight ratio of 20:10:35:35) on a flexible stretch film of polyvinyl chloride as a support.

A rectangular piece (1.5 cm×1.8 cm) of microporous cellulose ester (pore size: 0.6 μm, a product of Millipor) as a water-absorbing and adsorbent membrane was stuck on the above pressure-sensitive adhesive tape. Further, a square piece (1.8 cm×1.8 cm) of cellulose nitrate/cellulose acetate (pore size: 0.45 μm, a product of Millipor) as an adsorption carrier was stuck on the member. The surface of the carrier was covered with a polyethylene terephthalate film to give a sticking-type diagnostic preparation.

EXAMPLE 3
Diagnostic Patch having One-Layer Adsorption Carrier

A circular pressure-sensitive adhesive tape having a diameter of 4 cm was made by spreading a pressure-sensitive adhesive comprising SIS, polyisobutylene, ester gum, liquid paraffin and starch acrylate (at a weight ratio of 22:8:33:35:2) on a flexible stretch film of polyvinyl chloride as a support.

A circular piece (diameter: 2 cm) of cellulose nitrate/cellulose acetate (pore size: 1 μm, a product of Millipor) as an adsorption carrier was stuck on the above tape. The surface of the carrier was covered with a polyethylene terephthalate film.

EXAMPLE 4
Diagnostic Patch having Incorporation-Type Adsorption Carrier

A pressure-sensitive adhesive tape having an adsorptive power was made by spreading a pressure-sensitive adhesive comprising SIS, ester gum, liquid paraffin, aluminum silicate and powdery cellulose (at a weight ratio of 24:35:35:2:4) on a circular piece (diameter: 2 cm) of a flexible stretch film of polyvinyl chloride as a support. The tape was covered with a polyethylene terephthalate film to give a diagnostic patch.

EXAMPLES 5 TO 35

Diagnostic patch were made from the components (support, pressure-sensitive adhesive, water-absorbing and adsorbent member, adsorption carrier, adhesive and peelable cover) specified in Table 1 in the same manners as those of Examples 1 to 4.

TABLE 1

| | | Example | support | pressure-sensitive adhesive | water-absorbing and adsorbent member | adsorption carrier | adhesive | peelable cover |
|---|---|---|---|---|---|---|---|---|
| Two-layer adsorption carrier | adhesive bonding type | 5 | flexible stretch polyvinyl chloride film | SIS ester gum liquid paraffin | 20 pt. microporous cellulose 35 pt. pore size: 35 pt. 0.6 μm (product of Millipor) | cellulose nitrate/ cellulose acetate pore size: 0.25 μm (product of Millipor) | methyl acrylate-2-ethylhexyl acrylate copolymer | polyethylene terephthalate film |
| | | 6 | flexible stretch polyvinyl chloride film | SIS rosin ester liquid paraffin | 18 pt. microporous 25 pt. cellulose 57 pt. pore size: 0.6 μm (product of Millipor) | cellulose nitrate/ cellulose acetate pore size: 0.1 μm (product of Millipor) | polyvinyl alcohol | polyethylene terephthalate film |
| | | 7 | stretch urethane film | SIS terpene resin liquid paraffin | 18 pt. starch-45 pt. acrylic acid 37 pt. graft copolymer | cellulose nitrate/ cellulose acetate pore size: 1 μm (product of Millipor) | polyvinyl alcohol | polyethylene terephthalate film |
| | | 8 | woven fabric of stretch polyethylene terephthalate | SIS ester gum liquid paraffin polyisobutylene | 25 pt. starch-30 pt. acrylic acid 30 pt. graft 15 pt. copolymer | cellulose nitrate/ cellulose acetate pore size: 5 μm (product of Millipor) | methoxyethylene-maleic anhydride polymer | polyethylene terephthalate film |
| Two-layer adsorption carrier | adhesive bonding type | 10 | nonwoven fabric of stretch urethane fiber | SIS ester gum liquid paraffin polyisobutylene | 20 pt. crosslinked 30 pt. carboxymethyl-35 pt. cellulose 15 pt. | hydrophilic polyvinyldene fluoride pore size: 0.1 μm (product f Millipor) | polymvinyl alcohol | polyethylene terephthalate film |
| | | 11 | woven fabric of stretch polyethylene fiber | SIS rosin ester liquid paraffin | 17 pt. crosslinked 28 pt. carboxymethyl-55 pt. cellulose | hydrophilic polyvinylidene fluoride pore size: 0.45 μm (product of Millipor) | isobutylene-maleic anhydride copolymer | polyethylene terephthalate film |
| | | 12 | stretch urethane film | SIS rosin ester liquid paraffin aluminum silicate starch acrylate | 20 pt. microporous 35 pt. cellulose 35 pt. pore size: 2 pt. 0.6 μm (product of 3 pt. Millipor) | hydrophilic polyvinylidene fluoride pore size: 5 μm (product of Millipor) | methoxyethylene maleic anhydride copolymer | polyethylene terephthalate film |

TABLE 1-continued

| | | Example | support | pressure-sensitive adhesive | water-absorbing and adsorbent member | adsorption carrier | adhesive | peelable cover |
|---|---|---|---|---|---|---|---|---|
| | | 13 | stretch urethane film | SIS<br>rosen ester<br>liquid paraffin<br>polyacrylic acid salt | 15 pt. polysodium<br>22 pt. acrylate<br>53 pt.<br>10 pt. | polyvinylidene fluoride<br>pore size: 0.22 μm<br>(product of Millipor) | methyl acrylate-2-ethylhexyl acrylate copolymer | polyethylene terephthalate film |
| Two-layer adsorption carrier | adhesive bonding type | 14 | stretch ethylene-vinyl acetate copolymer film | SIS<br>rosin ester<br>liquid paraffin<br>starch-acrylic acid graft copolymer | 15 pt. polysodium<br>22 pt. acrylate<br>53 pt.<br>10 pt. | polyvinylidene fluoride<br>pore size: 0.22 μm<br>(product of Millipor) | acrylic acid-octyl acrylate copolymer | polyethylene terephthalate film |
| | | 15 | stretch urethane film | SIS<br>terpene resin<br>liquid paraffin | 20 pt. polysodium<br>42 pt. acrylate<br>38 pt. | microporous cellulose<br>pore size: 0.2 μm<br>(product of Millipor) | acrylic acid-octyl acrylate copolymer | polyethylene terephthalate |
| | | 16 | stretch polypropylene film | SIS<br>terpene resin<br>liquid paraffin | 20 pt. polysodium<br>42 pt. acrylate<br>38 pt. | microporous cellulose<br>pore size: 0.6 μm<br>(product of Millipor) | polyvinyl alcohol | polyethylene terephthalate |
| | | 17 | stretch ethylene-vinyl acetate copolymer film | SIS<br>ester gum<br>liquid paraffin<br>polyisobutylene | 20 pt. polysodium<br>37 pt. acrylate<br>33 pt.<br>10 pt. | cellulose nitrate<br>pore size: 0.1 μm<br>(product of Sartorius) | 2-ethyhexyl acrylate-vinylpyrrolidone copolymer | polyethylene terephthalate film |
| Two-layer adsorption carrier | adhesive bonding type | 18 | stretch polyethylene film | SIS<br>terpene ester<br>liquid paraffin<br>polyacrylic acid salt | 15 pt. polysodium<br>42 pt. acrylate<br>35 pt.<br>3 pt. | cellulose nitrate<br>pore size: 0.45 μm<br>(product of Sartorius) | 2-ethylhexyl acrylate-vinylpyrrolidone copolymer | polyethylene terephthalate film |
| | | 19 | stretch vinyl chloride film | SIS<br>rosin ester<br>liquid paraffin<br>starch-acrylic acid graft copolymer | 17 pt. polysodium<br>20 pt. acrylate<br>55 pt.<br>8 pt. | cellulose nitrate<br>pore size: 3 μm<br>(product of Sartorius) | n-butyl acrylate-methacrylic acid copolymer | polyethylene terephthalate film |
| | | 20 | stretch urethane film | SIS<br>rosin ester<br>liquid paraffin | 18 pt. starch-acrylic<br>29 pt. acid graft<br>53 pt. copolymer | cellulose nitrate<br>pore size: 0.2 μm<br>(product of Sartorius) | polyvinyl alcohol | polyethylene terephthalate film |
| | | 21 | nonwoven stretch polyethylene fabric | SIS<br>ester gum<br>liquid paraffin<br>polyisobutylene | 21 pt. starch-acrylic<br>34 pt. acid graft<br>30 pt. copolymer<br>15 pt. | cellulose acetate<br>pore size: 1.2 μm<br>(product of Sartorius) | methoxyethylene-maleic anhydride copolymer | polyethylene terephthalate film |
| Two-layer adsorption carrier | adhesive bonding type | 22 | stretch urethane film | natural rubber<br>polybutene<br>ester gum<br>zinc oxide | 20 pt. cellulose<br>20 pt. pore size:<br>35 pt. 3 μm<br>15 pt. (product of ADVANTEC TOYO) | nonwoven cotton fabric<br>pore size: 100 μm | isobutylene-maleic anhydride copolymer | polyethylene terephthalate film |
| | | 23 | flexible stretch polyvinyl chloride film | SIS<br>rosin ester<br>liquid paraffin<br>polyacrylic acide | 15 pt. cellulose<br>55 pt. pore size:<br>25 pt. 3 μm<br>5 pt. (product of ADVANTEC TOYO) | nonwoven nylon fabric<br>pore size: 80 μm | isobutylene-maleic anhydride copolymer | release paper |
| | | 24 | stretch urethane film | SIS<br>ester gum<br>liquid paraffin | 20 pt. crosslinked<br>55 pt. carboxymethyl-<br>25 pt. cellulose | nonwoven nylon fabric<br>pore size: 100 μm | acrylic acid-octyl arylate copolymer | release paper |
| | | 25 | stretch ethylene-vinyl acetate copolymer film | SIS<br>starch acrylate<br>liquid paraffin | 50 pt. crosslinked<br>3 pt. carboxymethyl-<br>47 pt. cellulose | polypropylene filter<br>pore size: 0.6 μm<br>(product of Millipor) | acrylic acid-octyl arylate copolymer | release paper |
| Two-layer adsorption carrier | adhesive bonding type | 26 | flexible stretch polyvinyl chloride film | SIS<br>ester gum<br>liquid paraffin<br>polyacrylic acid salt | 15 pt. polysodium<br>55 pt. acrylate<br>25 pt.<br>5 pt. | polypropylene filter<br>pore size: 0.6 μm<br>(product of Millipor) | polyvinyl alcohol | release paper |
| | | 27 | flexible stretch polyvinyl chloride film | SIS<br>ester gum<br>liquid paraffin | 20 pt. polysodium<br>55 pt. acrylate<br>25 pt. | woven polypropylene fabric<br>pore size: 100 μm | alginic acid | polyethylene terephthalate film |
| | | 28 | stretch polypropylene film | SIS<br>ester gum<br>liquid paraffin<br>polyacrylic acid salt | 15 pt. polysodium<br>55 pt. acrylate<br>25 pt.<br>5 pt. | woven polypropylene fabric<br>pore size: 1.5 μm | guar gum | polyethylene terephthalate film |

TABLE 1-continued

| | | Example | support | pressure-sensitive adhesive | water-absorbing and adsorbent member | adsorption carrier | adhesive | peelable cover |
|---|---|---|---|---|---|---|---|---|
| Two-layer adsorption carrier | separation type | 29 | flexible stretch film | SIS ester gum liquid paraffin polyisobutylene | 20 pt. microporous 35 pt. cellulose 35 pt. pore size: 10 pt. 0.6 μm (product of Millipor) | cellulose nitrate/ cellulose acetate pore size: 0.25 μm (product of Millipor) | — | polyethylene terephthalate film |
| | | 30 | stretch polyethylene terephthalate film | SIS rosin ester liquid paraffin | 18 pt. polysodium 25 pt. acrylate 57 pt. | cellulose nitrate/ cellulose acetate pore size: 1 μm (product of Millipor) | — | polyethylene terephthalate film |
| | | 31 | stretch urethane film | SIS terpene resin liquid paraffin | 18 pt. starch-acrylic 45 pt. acid graft 37 pt. colpolymer | microporous cellulose pore size: 0.45 μm (product of Millipor) | — | polyethylene terephthalate film |
| One-layer adsorption carrier | | 32 | flexible stretch polyvinyl chloride film | SIS polyisobuthylene liquid paraffin ester gum polyacrylic acid salt | 17 pt. cellulose nitrate/cellulose acetate 10 pt. pore size: 0.45 μm 27 pt. (product of Millipor) 30 pt. 13 pt. | | — | release paper |
| | | 33 | nonstretch vinyl acetrate film | SIS terpene resin liquid paraffin startch-acylic acid graft copolymer | 15 pt. nitrocellulose 40 pt. pore size: 1 μm 30 pt. (product of ADVANTEC TOYO) 15 pt. | | — | release paper |
| | | 34 | nonstretch polyethylene film | SIS ester gum liquid paraffin | 18 pt. ultrafine fiber 55 pt. (trade name: belima X, product of 27 pt. Kanebo, Ltd.) | | — | release paper |
| Incorporation-type adsorption carrier | | 35 | flexible stretch polyvinyl chloride film | SIS polyisobutylene liquid paraffin powdery cellulose nitrate/cellulose acetate polyacrylic acid salt | 16 pt. 32 pt. 32 pt. blending 10 pt. 10 pt. | | — | release paper |

EXAMPLE 36
Expression of Application Site

The alphabets "L" and "R" were printed each on two diagnostic patch (wherein the pressure-sensitive adhesive tape had an elliptic form (3 cm×4 cm) and the absorption carrier had a circular form having a diameter of 1.5 cm) made in the same manner as that of Example 1. Ten normal women were made to stick the printed patches on their nipples by themselves. All of them stuck the patch printed with the alphabet "L" on the left nipples, with the one printed with the alphabet "R" being stuck on their right nipples.

The words "up" and "down" were printed on a diagnostic patch made in the same manner as that of Example 1 to tell the upper side from the lower side. Ten normal men were made to stick the printed patch on the insides of their upper arms. All of them stuck the patch with the side printed with the word "up" set upward (i.e., with the side printed with the word "down" set downward).

From these results, the printing on the diagnostic patch was ascertained to be effective in telling the application site of the patch.

EXAMPLE 37
Color of Pressure-Sensitive Adhesive Tape

Diagnostic patches were made in the same manner as that of Example 4 except that a flexible polyvinyl chloride colored in flesh color or a translucent or transparent flexible polyvinyl chloride was used as the support. The normal men were each marked on the inside of upper arm and were made to stick the patches on the inside of upper arm by using the mark as a target. The patch having a translucent or transparent support could be stuck on the target site more accurately than that having a colored support. From these results, it was ascertained that the patch having a translucent or transparent support can be stuck more accurately than that having a colored support.

EXPERIMENTAL EXAMPLE 1

The diagnostic patches made in Examples 1 to 35 (wherein the pressure-sensitive adhesive tare had a circular form having a diameter of 3 cm and the adhesion carrier had a circular form having a diameter of 1.2 cm) were examined for the following items. The results are given in Table 2.
Hydrophilicity: at 25° C. under the pressure of 1 atom, each adsorption carrier was immersed in water to determine the wettability.

(criteria)
+: wetted
±: slightly wetted
−: not wetted at all

Adsorption: bovine serum albumin (BSA) dilutions having various concentrations were dropped onto each adsorption carrier and immobilized by drying. The resulting preparations were each immunostained with anti-BSA antibody to determine the amount of BSA adsorbed on the adsorption carrier.

(criteria)
++: 100 $\mu g/cm^2$ or above
+: 50 to 100 $\mu g/cm^2$
±: 0 to 50 $\mu g/cm^2$ Nonspecificity
Background: each patch was examined for nonspecific color development due to substances other than protein simultaneously with the above examination on adsorption.
Influence of sebum: patches were stuck on the insides of upper arms of ten normal men, allowed to stand for 24 hours, peeled therefrom, and subjected to immunostaining with anti-sIgA antibody.
(criteria)
  ++: pretty color-developed
  +: lightly color-developed
  ±: very lightly color-developed
  −: not color-developed
Skin irritation: the skin irritation of each patch was determined by sticking the patch on the insides of upper arms of ten healthy men, allowing it to stand for 24 hours, and peeling it.
(criteria)
  +: light erythema
  ±: very light erythema
  −: no erythema

TABLE 2

Results of performance rest of various diagnostic patches

| Ex. | Hydro-philicity | Adsorption | Nonspecific background | Stimulation |
|---|---|---|---|---|
| 1 | + | ++ | − | − |
| 2 | + | ++ | − | − |
| 3 | + | ++ | − | − |
| 4 | + | ++ | − | − |
| 5 | + | ++ | − | − |
| 6 | + | ++ | − | − |
| 7 | + | ++ | − | − |
| 8 | + | ++ | − | − |
| 9 | + | ++ | − | − |
| 10 | + | ± | − | − |
| 11 | + | ± | − | − |
| 12 | + | ± | − | − |
| 13 | ± | + | − | − |
| 14 | ± | + | − | − |
| 15 | ± | ++ | − | − |
| 16 | + | ++ | − | − |
| 17 | + | ± | − | − |
| 18 | + | ± | − | − |
| 19 | + | ± | − | − |
| 20 | + | ± | − | − |
| 21 | + | ± | − | − |
| 22 | + | ± | − | − |
| 23 | ± | ++ | ± | − |
| 24 | ± | ++ | ± | − |
| 25 | ± | ± | ± | − |
| 26 | ± | ± | ± | − |
| 27 | ± | ± | ± | − |
| 28 | ± | ± | ± | − |
| 29 | + | ++ | − | − |
| 30 | + | ++ | − | − |
| 31 | + | ++ | − | − |
| 32 | + | ++ | ± | − |
| 33 | + | ++ | ± | − |
| 34 | + | ± | − | − |
| 35 | + | ++ | ± | − |

As shown in Table 2, the dependence of adsorption of protein on the pore size and that thereof on the liquid permeability were evaluated.

With respect to the dependence of adsorption of protein on the pore size, a smaller pore generally gives a higher adsorption. However, when the pore is too small, the preparation will be clogged with BSA or fluid, while when it is too large, the color development of immunostaining will be loose to result in difficult macroscopic judgement. Accordingly, the pore size may range from 0.01 to 100 $\mu$m. In particular, when it lies with the range of 0.01 to 50 $\mu$m, better results can be attained.

With respect to the dependence of adsorption of protein on the liquid permeability, a patch made (as a control) by using a completely water-impermeable polyester paper (trade name: Purely 2025FL, a product of AWA paper MFG CO., LTD.).) as an adsorption carrier could not adsorb BSA, so that the adsorption carrier was not immunostained at all. On the other hand, a patch having an adsorption carrier of a liquid permeability (from (±) to (+)) was excellent in both adsorption of BSA and immunostaining properties. Accordingly, it is preferable that the adsorption carrier be a liquid-permeable one.

The followings turned out from the results of Table 2.

It is desirable that the pressure-sensitive adhesive be one which does not exert any adverse effect on the human body, does not hinder the reaction system, and exhibits readhesion properties.

It is desirable that the water-absorbing and adsorbent member be one having both a water-absorbing or retaining function and an adsorbent function.

It is desirable that the adsorption carrier be one which exhibits a high adsorption function, has pores (which serve to enlarge the surface area) and is permeable to liquid.

It is desirable that the adhesive be a water-permeable one.

EXPERIMENTAL EXAMPLE 2

Qualitative and Quantitative Assay

Method

CEA dilutions having concentrations ranging from 0 to 10 $\mu$g/ml were dropped on each of the diagnostic patches (wherein the pressure-sensitive adhesive tape had a circular form having a diameter of 5 cm and the adsorption carrier had a circular form having a diameter of 2 cm) made in the Examples 1 to 3, 5, 7, 15, 22 and 31 in an amount of 1 $\mu$l, blocked with milk protein, and reacted with anti-CEA antibody. The resulting system was treated with biotin-labeled antimouse Iq and a peroxidase-labeled avidin solution and color-developed with diaminobenzidine and hydrogen peroxide. The color development was stopped with 2 M sulfuric acid. The developed color due to CEA was measured macroscopically (qualitatively or semi-quantitatively) or with a densitometer (quantitatively). The results are given in Table 3.

TABLE 3

Qualitative and semiquantitative assay

| CEA | qualitative | | | | | | | | semiquantitative | | | | | | | | quantitative | | | | | | | |
|---|---|---|---|---|---|---|---|---|---|---|---|---|---|---|---|---|---|---|---|---|---|---|---|---|
| ng | 1 | 2 | 3 | 5 | 7 | 15 | 22 | 31 | 1 | 2 | 3 | 5 | 7 | 15 | 22 | 31 | 1 | 2 | 3 | 5 | 7 | 15 | 22 | 31 |
| 0 | − | − | − | − | − | − | − | − | − | − | − | − | − | − | − | − | 0 | 0 | 0 | 0 | 0 | 0 | 0 | 0 |
| 0.1 | + | + | + | + | + | + | + | + | ± | ± | ± | ± | ± | ± | ± | ± | 15 | 16 | 15 | 17 | 15 | 15 | 16 | 16 |
| 1 | + | + | + | + | + | + | + | + | + | + | + | + | + | + | + | + | 25 | 25 | 26 | 25 | 25 | 25 | 27 | 27 |
| 10 | + | + | + | + | + | + | + | + | ++ | ++ | ++ | ++ | ++ | ++ | ++ | ++ | 34 | 33 | 32 | 34 | 34 | 36 | 35 | 35 |

As apparent form the results of Table 3, CEA was color-developed depending upon the concentration thereof. Further, it was ascertained that the developed color due to CEA can be measured qualitatively, semiquantitatively or quantitatively.

EXPERIMENTAL EXAMPLE 3

Staining Result of Secretion from Normal Women

Method

Diagnostic patches of Example 6 (wherein the pressure-sensitive adhesive tape had an elliptic form (3 cm×4 cm) and the adsorption carrier had a circular form having a diameter of 2 cm) were stuck on the nipples of two healthy adult married women (aged 32 and 40), allowed to stand as such for 5 minutes, one hour, 24 hours or 48 hours, and thereafter peeled. The resulting patches were examined in the same manner as that of Experimental Example 2 qualitatively or semiquantitatively. The results are given in Table 4.

TABLE 4

Staining of secretion from healthy women

| Healthy | | Qualitative | | | | Semiquantitative | | | |
|---|---|---|---|---|---|---|---|---|---|
| adult | | 5 min | 1 hr | 24 hr | 48 hr | 5 min | 1 hr | 24 hr | 48 hr |
| A | right | − | − | − | − | − | − | − | − |
|   | left | − | − | − | − | − | − | − | − |
| B | right | − | − | − | − | − | − | − | − |
|   | left | − | − | − | − | − | − | − | − |

As shown in Table 4, no CEA was detected in the secretion from the nipple of each of the two healthy adult women.

EXPERIMENTAL EXAMPLE 4

Staining Result of Secretion from Patient with Mammary Cancer

Method

Two diagnostic patches made in the same manner as that of Example 1 were stuck on the both nipples of a patient A (aged 49) whose illness was diagnosed as mammary cancer of the right breast, allowed to stand for 24 hours and thereafter peeled. The resulting patches and a diagnostic patch for calibration having CEA immobilized thereon were subjected to blocking with milk protein, reaction with anti-CEA antibody, treatment with peroxidase-labeled antimouse Ig and color development using diaminobenzidine and hydrogen peroxide successively. The color development was stopped with 2 M sulfuric acid. The developed color due to CEA was measured qualitatively, semiquantitatively or quantitatively. The results are given in Table 5.

TABLE 5

Staining result of secretion from patient with mammary cancer

| | | Qualitative | Semiquantitative | Quantitative (ng/ml) |
|---|---|---|---|---|
| A | left | − | − | 0 |
|   | right | + | ++ | 9.5 |

As shown in Table 5, the diagnostic patch stuck on the right nipple was color-developed in dark brown in a spread state. On the other hand, the preparation stuck on the left nipple was not color-developed at all.

EXPERIMENTAL EXAMPLE 5

Judgement among Healthy Adult, Patient with Mastopathy and Patient with Mammary Cancer Method Diagnostic patches made in the same manner as that of Example 31 were stuck on the left and right nipples of nine healthy women and eight patients, allowed to stand as such for 24 hours and thereafter peeled. The resulting patches were immunostained in the same manner as that of Experimental Example 2. The results are given in Table 6 by the density of color.

TABLE 6

Judgement among healthy adult, patient with mastopathy and patient with mammary cancer

| | No. of samples | | Stain of CEA | | | | | | | |
|---|---|---|---|---|---|---|---|---|---|---|
| | | | 1 | 2 | 3 | 4 | 5 | 6 | 7 | 8 |
| Healthy woman | 9 | left | − | − | − | − | − | − | − | − |
| | | right | − | − | − | − | − | − | − | − |
| Mastopathy | 4 | left | − | + | − | − | | | | |
| | | right | − | − | ± | − | | | | |
| Mammary cancer (underlined) | 4 | left | ±±± | − | ±±± | − | | | | |
| | | right | − | ± | ± | ±± | | | | |

As shown in Table 6, medium to strong positive reactions were observed at sites affected by mammary cancer, while slight positive reactions were observed in some sites affected by mastopathy.

EXPERIMENTAL EXAMPLE 6

Immunoassay using Latexlabeled Antibody

Method

Blue latex (2%, particle size: 0.2 m) was added to a solution of antihuman CEA monoclonal antibody (mouse IgG1). The resulting mixture was reacted at 37° C. to give blue latex labeled antihuman CEA monoclonal antibody. Diagnostic patches made in the same manner as that of Example 7 were stuck on the nipples of a healthy adult woman (aged 36) and a patient (aged 45) with phyma-free mammary cancer at her left breast, allowed to stand as such for 24 hours and thereafter peeled. The resulting patches were immersed in a solution of the above latex-labeled antihuman CEA monoclonal antibody to make the solution permeate the patches. The results are given in Table 7.

TABLE 7

Amount of CEA as determined by immunoassay using latex-labeled antibody

| Sample | Site of application | Secretion of CEA | |
|---|---|---|---|
| | | No. of spots | density |
| A (healthy) | left nipple | 0 | – |
| | right nipple | 0 | – |
| B (patient) | left nipple | 3 | ++ |
| | right nipple | 0 | – |

As shown in Table 7, blue spots of dot form were observed only on the patch stuck on the left nipple of the patient with mammary cancer about one minute after the immersion of the sample in the antibody solution.

EXPERIMENTAL EXAMPLE 7
Immunoassay using Gold Colloid Labeled Antibody
Method

A gold colloid (20 nm, 10 ml) was reacted with optimal antihuman CEA monoclonal antibody for one hour, followed by the blocking with 1% bovine serum albumin. The resulting mixture was centrifuged at 8000×G for one hour to give antibody-sensitized gold colloid particles. A buffer was added to these particles to form a sensitized colloid dilution having an OD of 3.0 at 530 nm.

Diagnostic patches made in the same manner as that of Example 23 were stuck on the same woman and patient as those of Experimental Example 6 and thereafter assayed with the above colloid dilution. The results are given in Table 8.

TABLE 8

Amount of CEA as determined by immunoassay using gold colloid labeled antibody

| Sample | Site of application | Secretion of CEA | |
|---|---|---|---|
| | | No. of spots | density |
| A (healthy) | left nipple | 0 | – |
| | right nipple | 0 | – |
| B (patient) | left nipple | 3 | + |
| | right nipple | 0 | – |

As shown in Table 8, three spots were observed on the patch stuck on the left breast of the patient B at sites localized in the place corresponding to the outside of left breast, while the illness of the patient had been diagnosed clinically as cancer of the outside of left breast. Thus, this result agreed with the clinical symptom. It was ascertained from this agreement that the method of the present invention is useful.

EXPERIMENTAL EXAMPLE 8
Detection of Other Markers
Method

Diagnostic patches [having an elliptic pressure-sensitive adhesive tape (3 cm×4 cm) and a circular adsorption carrier (diameter: 1.5 cm)] made in the same manner as that of Example 1 were stuck on the nipples of a healthy adult married woman A (aged 40) and a patient B (aged 45) with mammary cancer (in her left breast), allowed to stand as such for 24 hours and thereafter peeled. The resulting patches were analyzed for the following markers. The results are given in Table 9.

Antigen-antibody reaction using monoclonal antibody against AFP, CA15-3 or erbB2
Detection of amino acid by ninhydrin reaction
Guaiac reaction of occult blood (detection of hemoglobin)
Detection of peroxidase (POD) and alkaline phosphatase (ALP) by enzyme reaction

TABLE 9

Detection of other markers

| | | APF | CA15-3 | erbB2 | amino acid | occult blood | POD | ALP |
|---|---|---|---|---|---|---|---|---|
| A | left | – | – | – | + | – | – | – |
| | right | – | – | – | + | – | – | – |
| B | left | +++ | +++ | ++ | +++ | + | ++ | ++ |
| | right | – | – | – | + | – | – | – |

As apparent from the results of Table 9, it was ascertained that various markers can be detected by the use of the diagnostic patch of the present invention.

EXPERIMENTAL EXAMPLE 9
Usefulness of the Diagnostic Patch
Method

A patient (aged 40) with mammary cancer (on her left breast) accompanied with the secretion from the nipple and one (aged 45) with mammary cancer (on her left breast) not accompanied therewith were made to apply diagnostic patches made in the same manner as that of Example 1 on their left nipples respectively. The patches were allowed to stand as such with the longest time of application being 24 hours. Separately, liquid-impermeable sheets (MAMMOTEC) having and CEA antibody immobilized thereon were brought into contact with the left nipples of the above patients and allowed to stand as such with the longest time of application being 24 hours.

The time of application or contact and the detection of CEA by immunostaining were evaluated. The results are given in Table 10.

TABLE 10

Usefulness of the diagnostic patch

| | Time of application or contact | | CEA | |
|---|---|---|---|---|
| | with secretion | without secretion | with secretion | without secretion |
| Preparation of Ex. 1 | 24 hrs | 24 hrs | ++ | ++ |
| Liquid-impermeable sheet | failure (1 min) | failure (1 min) | ± | – |

(In the above Table, "1 (or 2) min" means that the preparation could be retained at the affected site for one (or two) minute without shifting)

As apparent from the results of Table 10, the diagnostic patch could be retained for 24 hours without shifting and enabled the predetermination of a mammary gland affected with a cancer. Further, the patch could be retained on the affected site for a long time (24 hours), so that CEA could be detected by the use of the patch even from a patient with mammary cancer not accompanied with secretion.

On the other hand, the liquid-impermeable sheet could not be retained in the contact with the nipple for 24 hours, so that both of the sheets stuck on the patients shifted one or two minutes after the application. Further, the sheet failed in detecting CEA from a patient with mammary cancer not accompanied with the secretion from the nipple, though the sheet succeeded in detecting it from a patient with mammary cancer accompanied with the secretion therefrom.

EXPERIMENTAL EXAMPLE 10

Usage
Method

Diagnostic patches made in the same manner as that of Example 1 were stuck on the forehead, chest, inside of upper arm and flat of hand of each of five healthy adults. They were peeled 10 minutes, 6 hours and 24 hours after the sticking, and immunoassayed qualitatively by enzyme-labeled antibody technique. The area of application was changed variously depending upon the site of application. The results are given in Table 11.

TABLE 11

Usage and amount of secreted sIgA

| | Amt. of sIgA | | |
|---|---|---|---|
| | 10 min | 6 hrs | 24 hrs |
| forehead | + | ++ | +++ |
| chest | + | + | +++ |
| inside of upper arm | + | ++ | +++ |
| flat of hand | ± | + | ++ |

As shown in Table 11, one or more spots due to the secretion of sIgA were observed on the patch stuck on any of the above sites for any of the above times. Further, the assay could be conducted even when the area of application of the adsorption carrier ranged from several square millimeters to 10 square centimeters. In other words, it turned out that the area of application and the time of application need not be limited for the assay.

EXPERIMENTAL EXAMPLE 11

Qualitative Assay-Enzyme Labeled Antibody Technique
Method

A diagnostic patch made in the same manner as that of Example 2 was stuck on a healthy adult man and peeled. The resulting patch was reacted with antihuman sIgA monoclonal antibody (mouse IgGl) for 20 hours and subjected to the blocking with bovine serum albumin and the reaction with peroxidase-labeled antimouse IgG antibody (rabbit) successively. The color development of the preparation was begun by adding a mixture comprising a 0.25 mg/ml solution of diaminobenzidine and a 0.0125% solution of hydrogen peroxide at a volume ratio of 1:1, and 3 minutes thereafter, stopped by the addition of a 2 M solution of sulfuric acid.

There gas observed a brown spot of dot form presumably due to the sIgA secreted along the sweat gland.

EXPERIMENTAL EXAMPLE 12

Quantitative Assay-Enzyme Labeled Antibody Technique
Method

The sticking-type diagnostic patches of Example 6 which had been stuck on four healthy adult men and peeled were reacted with antihuman sIgA monoclonal antibody (mouse IgGl) for 2 hours. The resulting patches were subjected to the blocking with bovine serum albumin and the reaction with peroxidase-labeled antimouse IgG antibody (rabbit). The color development of the patches was begun by adding a mixture comprising a 1.5 mg/ml solution of O-phenylenediamine and a 1% solution of hydrogen peroxide at a volume ratio of 1:1, and 3 minutes thereafter, stopped by the addition of a 1% solution of sulfuric acid. The resulting patches were examined quantitatively for absorbance at 490 nm by the use of a spectrophotomer. The standard calibration curve of sIgA was shown in Table 12, while the amounts of skin sIgA secreted from the healthy adult men are give in Table 13.

TABLE 12

Calibration curve of sIgA

| Amt. of sIgA (ng/ml) | OD 490 nm |
|---|---|
| 0 | 0 |
| 0.1 | 0.18 |
| 1.0 | 0.33 |
| 10.0 | 0.53 |
| 100.0 | 0.70 |

TABLE 13

Amounts of sIgA secreted from healthy men

| Sample | Amt. of sIgA secreted (ng/ml) |
|---|---|
| A (healthy) | 0.12 |
| B (healthy) | 0.08 |
| C (healthy) | 0.54 |
| D (healthy) | 0.31 |

The quantitative analysis of the patch for sIgA is enabled by employing the calibration curve shown in Table 12.

EXPERIMENTAL EXAMPLE 13

Qualitative Assay-Latex Labeled Antibody Technique
Method

Blue latex (2%, particle size: 0.2 μm) was added to a solution of antihuman sIgA monoclonal antibody (mouse IgGl). The resulting mixture was reacted at 37° C. to prepare blue latex labeled antihuman sIgA monoclonal antibody. Diagnostic patches (having a circular pressure-sensitive adhesive tore (diameter: 3 cm) and a square adsorption carrier (1.5 cm)) prepared in the same manner as that of Example 1 were stuck on the chests of two healthy adults, a patient with atopic dermatitis and a patient with an infectious disease, allowed to stand as such for 5 minutes, peeled and immersed in a solution of the above latex labeled antihuman sIgA monoclonal antibody to make the solution permeate the preparations. The results are given in Table 14.

TABLE 14

Amount of sIgA determined by immunoassay using latex-labeled antibody

| Sample | Amt. of sIgA secreted |
|---|---|
| A (healthy man) | ++ |
| B (healthy woman) | ++ |
| C (patient with atopic dermatitis) | − |

TABLE 14-continued

Amount of sIgA determined by immunoassay using latex-labeled antibody

| Sample | Amt. of sIgA secreted |
|---|---|
| D (patient with infectious disease) | − |

As apparent from the results of Table 14, blue spots of dot form were observed about one minute after the immersion of the sample in the antibody solution. This result agreed with that of Experimental Example 11. Thus, it was ascertained that the immunoassay using the patch of the present invention exhibits good reproducibility.

EXPERIMENTAL EXAMPLE 14

Assay-Immunochromatography using Latex-Labeled Antibody

Method

Blue latex labeled antihuman sIgA monoclonal antibody prepared in the same manner as that of Experimental Example 13 was immobilized on part of a nitrocellulose film preliminarily blocked with 1% bovine serum slbumin, followed by further blocking. Only the area of the film wherein the antibody was immobilized was covered with a tape and the whole of the resulting film was further covered with a supporting tape to give a sticking-type diagnostic preparation. The patches thus made were stuck on the chests of the same healthy adults and patients as those of Experimental Example 13, allowed to stand as such for 20 minutes and peeled. The resulting patches were immersed in a physiological salt solution with the labeled antibody layer set downward. The results are given in Table 15.

TABLE 15

Amount of sIgA as determined by immunochromatography using blue latex labeled antibody

| Sample | Amt. of sIgA secreted |
|---|---|
| A (healthy man) | ++ |
| B (healthy woman) | ++ |
| C (patient with atopic dermatitis) | − |
| D (patient with infectious disease) | ± |

As apparent from the results of Table 15, blue spots appeared 2 minutes after the immersion of the patch. These results were nearly equivalent to those of Experimental Example 13.

EXPERIMENTAL EXAMPLE 15

Amounts of sIgA Secreted from Healthy Adults and Patients with Atopic Dermatitis Method Diagnostic patches made in the same manner as that of Example 2 were stuck on the insides of upper arms of 19 healthy adults and 19 patients with atopic dermatitis, allowed to stand as such for 24 hours and thereafter peeled. The resulting patches were immunostained in the same manner as that of Experimental Example 12. The results are given in Table 16.

TABLE 16

Amount of sIgA secreted from patients with atopic dermatitis

| | No. of samples | Amt. of sIgA secreted |
|---|---|---|
| Normal person | 19 | 9.84 ± 1.90 |
| patient with atopic dermatitis | 19 | 3.89 ± 0.95* |

(*: $p<0.05$)
(average ± S.E., in unit)

As apparent from the results of Table 16, the amounts of sIgA secreted from the patients with atopic dermatitis were smaller than those secreted from the normal persons. Accordingly, the diagnosis of atopic dermatitis can be conducted by assaying the amount of sIgA secreted from the skin.

INDUSTRIAL APPLICABILITY

The present invention, which has been described, has the following effects:

(1) The diagnostic patch of the present invention can be noninvasively and easily stuck on any site in a short time. Further, the preparation is little irritant to the skin and causes small adverse effects such as rash even when applied for a long time, being extremely safe.

(2) The diagnostic patch of the present invention can trap too small an amount of tumor markers secreted from the nipple to be samples as liquid by the technique of the prior art. Since the markers trapped by the patch can be assayed specifically, easily and quantitatively or qualitatively, the patch permits assay of many items.

In the qualitative assay of a tumor marker represented by CEA, judgement can be conducted with the naked eye only several minutes after the peeling of the patch, so that the assay of the marker can be conducted speedily and easily at the site of medical service. Further, the assay of CEA or other marker is useful for the diagnosis of mammary cancer, and particularly enables the mass screening or examination of early mammary cancer free from phyma. Furthermore, the patch enables the predetermination of primary focus of mammary cancer based on the site of a spot on the patch. Thus, the patch may bring about an increase in the diagnosis efficiency of mammary cancer.

(3) The sIgA secreted from the skin can be specifically, easily and qualitatively or quantitatively assayed by the use of the diagnostic patch of the present invention, though the sIgA is too little to be sampled as liquid by the technique of the prior art. In the qualitative assay of sIgA, particularly, judgement can be conducted with the naked eye only several minutes after the peeling of the patch, so that the assay of sIgA can be conducted speedily and easily at the site of medical service. Accordingly, the assay of sIgA with the patch of the present invention is useful for the diagnosis of atopic dermatitis.

Accordingly, the diagnostic patch for mammary cancer or atopic dermatitis according to the present invention and the method for the diagnosis thereof according to the present invention can be suitably used in the diagnosis of mammary cancer or atopic dermatitis.

What is claimed is:

1. A diagnostic patch for adsorbing a substance secreted from a living body comprising a support, said support being a transparent or translucent one having an expression for discrimination made thereon and having a surface, a pressure-sensitive adhesive spread over at least a part of said surface of said support, and a liquid permeable adsorption carrier which is stuck on said pressure-sensitive adhesive, said adsorption carrier adsorbing said substance and having a pore size of 0.01 to 100 μm.

2. A diagnostic patch for adsorbing a substance secreted from a living body comprising a support, said support having a surface, a pressure-sensitive adhesive spread over at least a part of said surface of said support, a liquid-permeable adsorption carrier which is stuck on said pressure-sensitive adhesive, said adsorption carrier adsorbing said substance and having a pore size of 0.01 to 100 μm, and a water-absorbing and adsorbent member, said water-absorbing and adsorbent member being made of at least one member selected from the group consisting of polyacrylic acid, salts of polyacrylic acid, isobutylene-maleic acid copolymer, starch-acrylic acid graft copolymer, polyethylene oxide, saponified vinyl acetate-unsaturated dicarboxylic acid copolymer, carboxymethylcellulose, saponified starch-acrylic acid graft copolymer, alginate, cellulose, carboxymethylcellulose, carboxymethylcellulose salts, hydroxyethylcellulose, hydroxypropylcellulose, methylcellulose, ethylcellulose, carboxymethylethylcellulose, hydroxypropylmethylcellulose, ethylhydroxyethylcellulose, cellulose acetate, cellulose nitrate, cellulose acetate phthalate, hydroxypropylmethylcellulose phthalate, poly-2-hydroxyethyl methacrylate, polyacrylic acid, polyvinyl alcohol-polyacrylic acid composite, polyurethane, polyester, polyethylene, polyvinyl chloride, filter paper and cloths.

3. A diagnostic patch for adsorbing a substance secreted from a living body comprising a support, said support having a surface, a pressure-sensitive adhesive spread over at least a part of said surface of said support, a liquid-permeable adsorption carrier which is stuck on said pressure-sensitive adhesive, said adsorption carrier adsorbing said substance and having a pore size of 0.01 to 100 μm, and a water-absorbing and adsorbent member being incorporated in said pressure-sensitive adhesive wherein said water-absorbing and adsorbent member is made of at least one member selected from the group consisting of polyacrylic acid, salts of polyacrylic acid, isobutylene-maleic acid copolymer, starch-acrylic acid graft copolymer, polyethylene oxide, saponified vinyl acetate-unsaturated dicarboxylic acid copolymer, carboxymethylcellulose, saponified starch-acrylic acid graft copolymer, alginate, cellulose, carboxymethylcellulose, carboxymethylcellulose salts, hydroxyethylcellulose, hydroxypropycellulose, methylcellulose, ethylcellulose, carboxymethylethylcellulose, hydroxypropylmethylcellulose, ethylhydroxyethylcellulose, cellulose acetate, cellulose nitrate, cellulose acetate phthalate, hydroxypropylmethylcellulose phthalate, poly-2-hydroxyethyl methacrylate, polyacrylic acid, polyvinyl alcohol-polyacrylic acid composite, polyurethane, polyester, polyethylene, polyvinyl chloride, filter paper and cloths and an additional adhesive adheres to said member, said adsorption carrier being bonded to said additional adhesive.

4. A diagnostic patch for adsorbing a substance secreted from a living body comprising a support, said support having a surface, a pressure-sensitive adhesive spread over at least a part of said surface of said support, a liquid-permeable adsorption carrier which is stuck on said pressure-sensitive adhesive, said adsorption carrier adsorbing said substance and having a pore size of 0.01 to 100 μm, and a water-absorbing and adsorbent member stuck on said pressure-sensitive adhesive wherein said water-absorbing and adsorbent member is made of at least one member selected from the group consisting of polyacrylic acid, salts of polyacrylic acid, isobutylene-maleic acid copolymer, starch-acrylic acid graft copolymer, polyethylene oxide, saponified vinyl acetate-unsaturated dicarboxylic acid copolymer, carboxymethylcellulose, saponified starch-acrylic acid graft copolymer, alginate, cellulose, carboxymethylcellulose, carboxymethylcellulose salts, hydroxyethylcellulose, hydroxypropylcellulose, methylcellulose, ethylcellulose, carboxymethylethylcellulose, hydroxypropylmethylcellulose, ethylhydroxyethylcellulose, cellulose acetate, cellulose nitrate, cellulose acetate phthalate, hydroxypropylmethylcellulose phthalate, poly-2-hydroxyethyl methacrylate, polyacrylic acid, polyvinyl alcohol-polyacrylic acid composite, polyurethane, polyester, polyethylene, polyvinyl chloride, filter paper and cloths, said adsorption carrier being laminated on said water absorbing and adsorption member.

5. The diagnostic patch as set forth in claim 1 wherein the pore size of said adsorption carrier is 0.01 to 50 μm.

6. The diagnostic patch as set forth in claim 2 wherein the pore size of said adsorption carrier is 0.01 to 50 μm.

7. The diagnostic patch as set forth in claim 3 wherein the pore size of said adsorption carrier is 0.01 to 50 μm.

8. The diagnostic patch as set forth in claim 4 wherein the pore size of said adsorption carrier is 0.01 to 50 μm.

9. The diagnostic patch as set forth in claim 1 wherein said adsorption carrier is made of at least one member selected from the group consisting of a cellulose derivative, porous gels, fibrous matrixes, paper, cloth and ceramics and wherein said cellulose derivative constituting said adsorption carrier is at least one member selected from the group consisting of cellulose, carboxymethylcellulose, carboxymethylcellulose salts, hydroxyethylcellulose, hydroxypropylcellulose, methylcellulose, ethylcellulose, carboxymethylethylcellulose, hydroxypropylmethylcellulose, ethylhydroxyethylcellulose, cellulose acetate, cellulose nitrate, cellulose acetate phthalate and hydroxypropylmethylcellulose phthalate.

10. The diagnostic patch as set forth in claim 2 wherein said adsorption carrier is made of at least one member selected from the group consisting of a cellulose derivative, porous gels, fibrous matrixes, paper, cloth, ceramics and wherein said cellulose derivative constituting said adsorption carrier is at least one member selected from the group consisting of cellulose, carboxymethylcellulose, carboxymethylcellulose salts, hydroxyethylcellulose, hydroxypropylcellulose, methylcellulose, ethylcellulose, carboxymethylethylcellulose, hydroxypropylmethylcellulose, ethylhydroxyethylcellulose, cellulose acetate, cellulose nitrate, cellulose acetate phthalate and hydroxypropylmethylcellulose phthalate.

11. The diagnostic patch as set forth in claim 3 wherein said adsorption carrier is made of at least one member selected from the group consisting of a cellulose derivative, porous gels, fibrous matrixes, paper, cloth and ceramics and wherein said cellulose derivative constituting said adsorption carrier is at least one member selected from the group consisting of cellulose, carboxymethylcellulose, carboxymethylcellulose salts, hydroxyethylcellulose, hydroxypropylcellulose, methylcellulose, ethylcellulose, carboxymethylethylcellulose, hydroxypropylmethylcellulose, ethylhydroxyethylcellulose, cellulose acetate, cellulose nitrate, cellulose acetate phthalate and hydroxypropylmethylcellulose phthalate.

12. The diagnostic patch as set forth in claim 4 wherein said adsorption carrier is made of at least one member selected from the group consisting of a cellulose derivative, porous gels, fibrous matrixes, paper, cloth and ceramics and wherein said cellulose derivative constituting said adsorption carrier is at least one member selected from the group consisting of cellulose, carboxymethylcellulose, carboxymethylcellulose salts, hydroxyethylcellulose, hydroxypropylcellulose, methylcellulose, ethylcellulose, carboxymethylethylcellulose, hydroxypropylmethylcellulose, ethylhydroxyethylcellulose, cellulose acetate, cellulose nitrate, cellulose acetate phthalate and hydroxypropylmethylcellulose phthalate.

13. The diagnostic patch as set forth in claim 1 wherein said support is a member selected from the group consisting of paper, cloth, nonstretchable or stretchable films made of a polyester resin, silicone resin, urethane resin, polyethylene resin, ethylene-vinyl acetate copolymer, flexible polyvinyl chloride and an aluminum foil and has a releasable cover attached to said adsorption carrier.

14. The diagnostic patch as set forth in claim 2 wherein said support is a member selected from the group consisting of paper, cloth, nonstretchable or stretchable films made of a polyester resin, silicone resin, urethane resin, polyethylene resin, ethylene-vinyl acetate copolymer, flexible polyvinyl chloride and an aluminum foil and has a releasable cover attached to said adsorption carrier.

15. The diagnostic patch as set forth in claim 3 wherein said support is a member selected from the group consisting of paper, cloth, nonstretchable or stretchable films made of a polyester resin, silicone resin, urethane resin, polyethylene resin, ethylene-vinyl acetate copolymer, flexible polyvinyl chloride and an aluminum foil and has a releasable cover attached to said adsorption carrier.

16. The diagnostic patch as set forth in claim 4 wherein said support is a member selected from the group consisting of paper, cloth, nonstretchable or stretchable films made of a polyester resin, silicone resin, urethane resin, polyethylene resin, ethylene-vinyl acetate copolymer, flexible polyvinyl chloride and an aluminum foil and has a releasable cover attached to said adsorption carrier.

17. A method for the diagnosis of mammary cancer including cancer free of phyma comprises applying a diagnostic patch according to claim 2 to a breast of a living body including nipples, said diagnostic patch adsorbing a substance secreted from said living body, keeping said patch adhering to the breast of said living body for a predetermined period of time, making a papillary secretion adsorbed and immobilized on said adsorption carrier, then peeling said patch, wherein the papillary secretion is a tumor-associated antigen or tumor marker selected from the group consisting of carcinoembryonic antigen, melanoma cell, melanoma marker, neuroblastoma, malignin, α-fetoprotein, pepsinogen, basic fetoprotein, fetoprealbumin, carbohydrate antigen, pancreatic cancer associated antigen, cancer antigen, squamous cell carcinoma, seminoprotein, prostate-specific antigen, ferritin and then conducting the assay of said papillary secretion adsorbed to determine the presence of mammary cancer.

18. A method for the diagnosis of atopic dermatitis, which comprises applying a diagnostic patch to the skin, mucosa or affected site of a human body, said diagnostic patch adsorbing secretory immunoglobulin A secreted from a living body and comprising a support, said support having a surface, a pressure-sensitive adhesive spread over at at least a part of said surface of said support, and a liquid-permeable adsorption carrier which is stuck on said pressure-sensitive adhesive, said adsorption carrier adsorbing said secretory immunoglobulin A and having a pore size of 0.01 to 100 μm, making a secretion therefrom adsorbed and immobilized on said adsorption carrier and then analyzing the secretion adsorbed for said secretory immunoglobulin A by immunoassay to determine the presence of atopic dermatitis.

* * * * *